United States Patent
Carriere Lluch (10) Patent No.: US 7,985,070 B2
(45) Date of Patent: Jul. 26, 2011

(54) SEGMENTAL DISTALISATION ELEMENT FOR ORTHODONTIC TREATMENTS

(76) Inventor: Luis Carriere Lluch, Barcelona (ES)

( * ) Notice: Subject to any disclaimer, the term of this patent is extended or adjusted under 35 U.S.C. 154(b) by 0 days.

(21) Appl. No.: 11/279,964

(22) Filed: Apr. 17, 2006

(65) Prior Publication Data

US 2006/0188833 A1 Aug. 24, 2006

Related U.S. Application Data (63) Continuation of application No. PCT/ES2004/000459, filed on Oct. 21, 2004.

(30) Foreign Application Priority Data

Oct. 23, 2003 (ES) .................... 200302472

(51) Int. Cl.
A61C 3/00 (2006.01)
(52) U.S. Cl. ......................................... 433/18
(58) Field of Classification Search ............... 433/7, 17, 433/18, 19, 23
See application file for complete search history.

(56) References Cited

U.S. PATENT DOCUMENTS

| 787,861 | A | * | 4/1905 | Shelp | 433/12 |
|---|---|---|---|---|---|
| 3,162,948 | A | * | 12/1964 | Gerber | 433/7 |
| 4,483,674 | A | | 11/1984 | Schutz | |
| 4,490,112 | A | * | 12/1984 | Tanaka et al. | 433/20 |
| 4,708,646 | A | * | 11/1987 | Jasper | 433/19 |
| 4,795,342 | A | * | 1/1989 | Jones | 433/19 |
| 4,871,310 | A | * | 10/1989 | Vardimon | 433/19 |
| 5,183,388 | A | * | 2/1993 | Kumar | 433/19 |
| 5,299,935 | A | | 4/1994 | Lokar | |
| 5,310,340 | A | * | 5/1994 | Zedda | 433/8 |
| 5,632,618 | A | * | 5/1997 | Jensen | 433/19 |
| 5,752,823 | A | * | 5/1998 | Vogt | 433/19 |
| 5,846,074 | A | * | 12/1998 | Klapper | 433/19 |
| 5,873,715 | A | | 2/1999 | Liou | |
| 5,897,313 | A | * | 4/1999 | Cleary et al. | 433/19 |
| 5,967,772 | A | * | 10/1999 | Gray | 433/7 |
| 6,120,289 | A | * | 9/2000 | Cleary et al. | 433/22 |
| 6,626,665 | B1 | | 9/2003 | Keles | |
| 6,976,839 | B2 | | 12/2005 | Lluch | |
| 2003/0064344 | A1 | * | 4/2003 | Vazquez | 433/19 |
| 2003/0091952 | A1 | * | 5/2003 | Bowman et al. | 433/18 |
| 2007/0218415 | A1 | | 9/2007 | Lluch | |

FOREIGN PATENT DOCUMENTS

| EP | 0931518 A1 | 7/1999 |
|---|---|---|
| ES | 2049306 | 4/1994 |
| WO | WO-01/39688 A1 | 6/2001 |
| WO | WO-03/028575 A2 | 4/2003 |

OTHER PUBLICATIONS

International Search Report for International Application No. PCT/ES2004/000459, dated Jan. 20, 2005.

* cited by examiner

*Primary Examiner* — Cris L Rodriguez
*Assistant Examiner* — Sunil K Singh
(74) *Attorney, Agent, or Firm* — Maier & Maier, PLLC (57) ABSTRACT

The segmental distalization element includes a smoothly arcuate central body equipped at one end with a head for adaptation to the canine and at the other end with a head for adaptation to the molar, connected to the arcuate body of the element via a zone of reduced cross-section to increase the resilience of the distalization element in the zone and obtain direct, easy adaptation.

21 Claims, 8 Drawing Sheets

SEGMENTAL DISTALISATION ELEMENT FOR ORTHODONTIC TREATMENTS

This application is a continuation of PCT International Patent Application No. PCT/ES2004/000459, filed Oct. 21, 2004, which claims priority of Spanish Patent Application No. 20030272, filed Oct. 23, 2003, both of which are incorporated by reference herein. PCT International Application No. PCT/ES2004/000459 was published in Spain on May 6, 2005 as Publication No. WO/2005/039432.

The present invention discloses an element for the segmental distalization of the canine-to-molar posterior maxillary sector for orthodontic treatments which affords significant advantages over the currently known elements for this purpose.

Auxiliary elements for segmental distalization are known in this art, for example those corresponding to Spanish patent application No. 200102210 in the name of the same applicant.

With the auxiliary element for segmental distalization according to the aforementioned patent in the name of the same applicant there was disclosed the formation of said auxiliary element in two parts, namely a median segment equipped with an enlargement intended to be fixed to the canine by means of adhesive and an arcuate arm ending with a ball which is introduced into a small arcuate receiving shoe fixed to the upper molar by adhesive.

Although the invention according to the aforementioned patent represented a significant advance over formerly known devices, it had specific problems owing to its production in two parts due to the relative production costs and the relatively awkward handling of the two-part assembly.

The inventor carried out research to obtain novel improvements to segmental distalization devices and arrived at the present invention.

As the fruit of the investigations and tests, the inventor has developed the present distalization device of which a specific characteristic is the single-part construction, the ease of adaptation thereof owing to inherent design characteristics and the production thereof from a metallic material which is preferably of the type known as super-resilient or a thermoelastic material which has the necessary characteristics of adequate toughness and resilience.

Basically, the new segmental distalization element is characterized in that it comprises a single-part elongate body having, at one end, a terminal which can be adapted to the external surface of the canine and which has an attachment for the resilient means, while the other end has, with interposition of a zone of greater flexibility, a shoe which can be coupled to the molar of the upper portion, preferably by an adhesive or other means.

In a preferred solution, the zone of greater resilience will consist of a simultaneous double elbow with a constriction of the material cross-section.

The portion with a double elbow and constriction is characterized in that it has two successive angle folds and at the same time a constriction of the cross section of the material between the central portion of the distalization element and the end or terminal for coupling to the molar. The first of the angles, in other words the angle which connects the intermediate elbow to the main element or arcuate bridge of the distalization element will preferably be an obtuse angle while the second angle, in other words the angle between the intermediate bridge of smaller cross-section and the end shoe for application to the molar, can be a slightly obtuse or right angle. The angle between the end of the central arm of the device and the longitudinal axis of the shoe for fixing to the canine will also be of interest for defining the structure of the distalization element according to the present invention.

The zone equipped with a constriction and which has two successive angles will preferably have a significant constriction and can similarly be formed by two fine parallel arms which define an intermediate aperture or other similar form.

However, the zone of greater flexibility preceding the element which can be adapted to the molar may be produced in a wide variety of forms and not necessarily with the double elbow provided for the preferred embodiment. Thus, for example, instead of a double elbow, a smooth curved zone, an omega like or similarly shaped zone with an open or closed shape, or a zone with one or more helical turns in an arrangement resembling a helical spring may be provided.

The accompanying drawings of a preferred embodiment of the invention, given as non-limiting examples, will assist the understanding thereof.

FIG. 9 shows a variation in which the portion of greater resilience has a smaller cross-section and a substantially curved sinusoidal or omega-shaped form or the like.

FIG. 10 shows a second variation in which the more flexible portion forms a closed omega-shaped handle or the like.

As shown in the drawings, the distalization element according to the present invention comprises, in a single part, a smoothly arcuate main body 1 of substantial length which terminates at one end with a head 2 for fixing it to the canine and at the other end with a head 3 for fixing it to the molar on the same side, having respective curved internal zones 4 and 5 for better adaptation to the canine and molar respectively and a variable number of reliefs such as the ribs 6 and 7, grating profiles, grids or other types of roughness intended to improve the fixing to the aforementioned tooth parts using an adhesive.

The distalization element according to the present invention has the basic characteristic of comprising a more flexible zone preferably in the form of a curved, constricted zone in various dispositions. In a preferred embodiment, said more flexible zone will adopt the form of a double-elbow connecting bridge 8 between the central arm 1 and the end head 3 for adaptation to the molar. Said double-elbow-shaped bridge or zone will also have a significant reduction in the material cross-section, resulting in significant flexibility in the end zone 3 which will allow better adaptation thereof and will therefore allow the production of the distalization segment in a single part.

The double elbow will be produced by means of a first, preferably obtuse, angle 9 and a second slightly obtuse or else right angle 10. In addition to said angles, of which the first is indicated by the letter .alpha., the angle .beta. will also be important, this angle being formed between the axis 11 of the end 12 of the arm 1 and the axis 13 which substantially corresponds to the longitudinal axis of the head 3 which preferably adopts the form of a small shoe 14 of rectangular or oval construction.

It will be appreciated that, despite the aforementioned quantities relating to the angles of the double elbow, the values of the angles can vary within wide limits, according to the prerequisites of the distalization device.

Figures 1, 2:
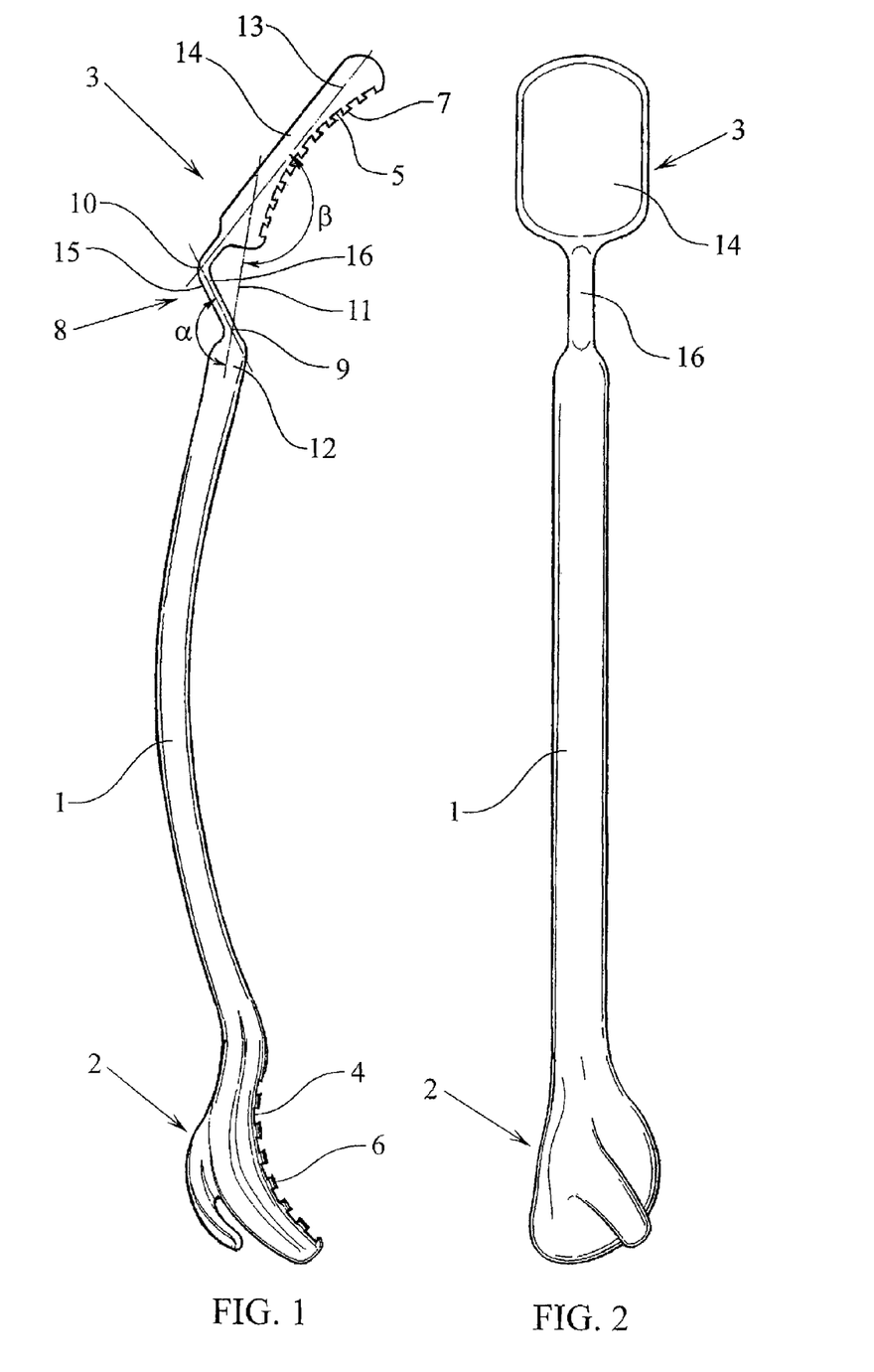
FIG. 1 is a lateral elevation of a distalization segment according to the present invention.
FIG. 2 is a front elevation of the actual segment.
Figure 3:
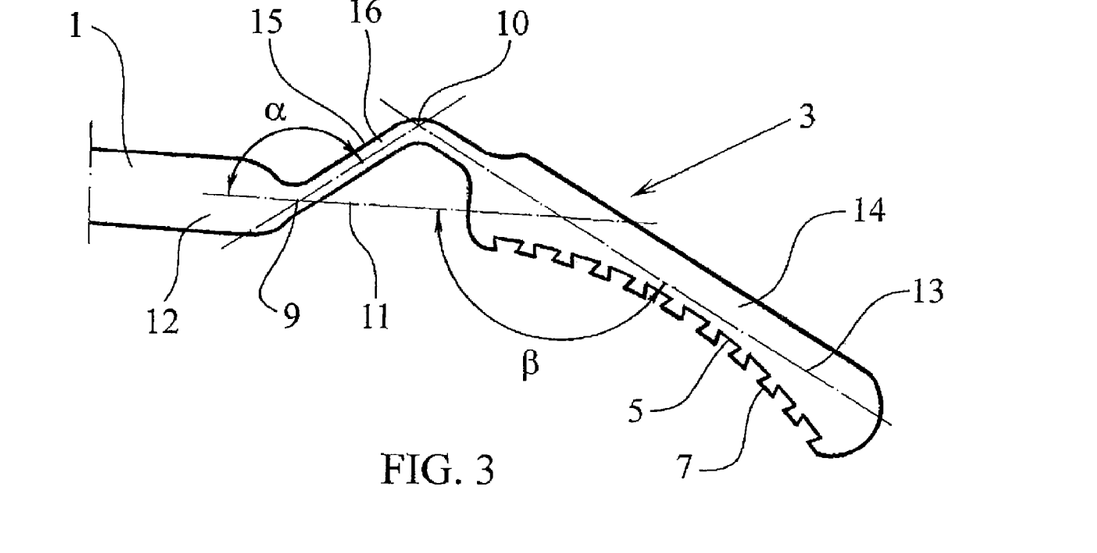
FIG. 3 is an elevation showing a detail of the double elbow at the end corresponding to the fixing to the molar.
Figure 4:
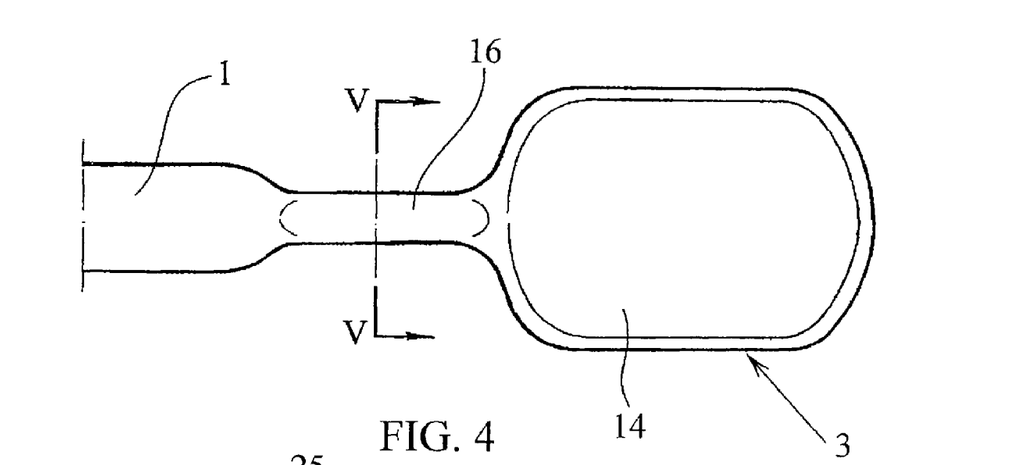
FIG. 4 is a plan view of the elements shown in FIG. 3.
Figure 5:
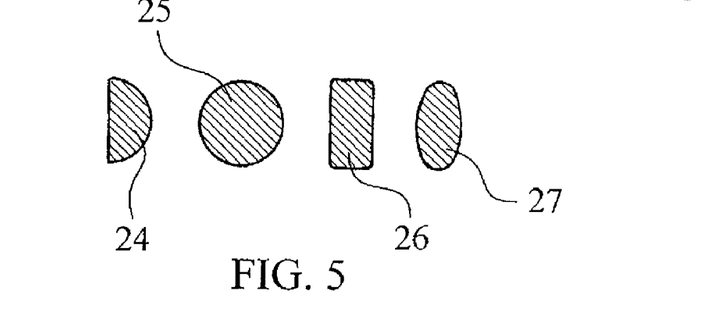
FIG. 5 is a cross-section through the sectional plane indicated with various alternative shapes.
Figure 6:
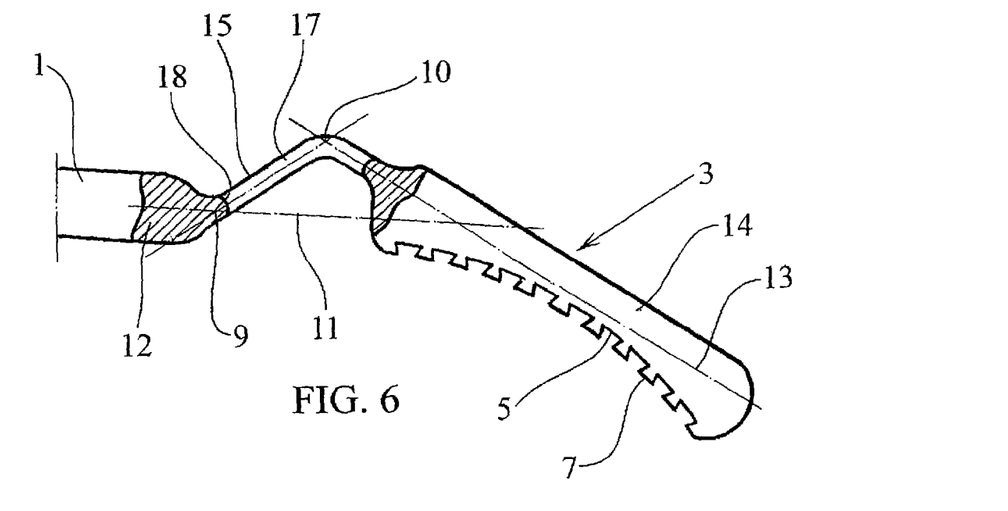
FIGS. 6, 7 and 8 are views similar to FIGS. 3, 4 and 5 for the version of elbowed zone with an intermediate window.
Figure 7:
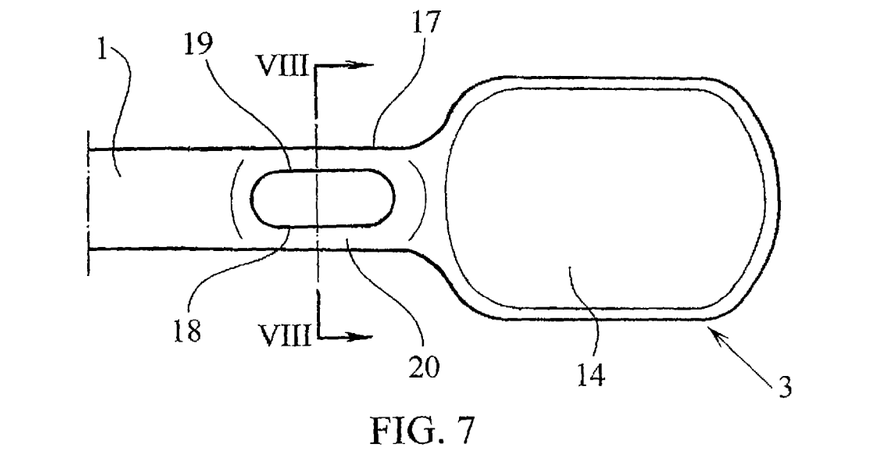
Figure 8:
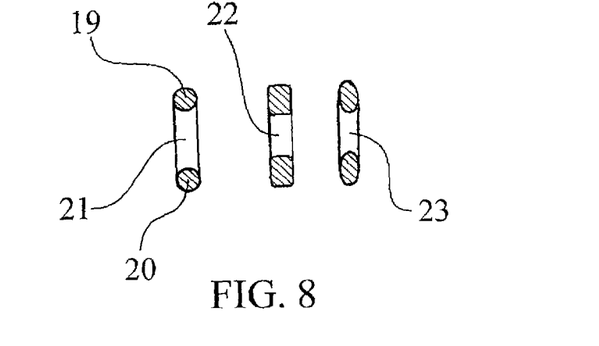

As mentioned, the zone of the double elbow, which is indicated by reference numeral 15, has a significant constriction with respect to the central portion 1, which can either be achieved by a constriction in cross-section as shown in FIGS. 1 and 2 to form a single connecting bridge between the central element or arm 1 and the end head 14 or be formed by means of a constricted zone 17, FIGS. 6 and 7, which will also have a central aperture 18 determining parallel arms 19 and 20 of which the precise shape can vary greatly, FIG. 8 showing three versions in which the first one 21 has two arms with a circular cross-section, the second, indicated by reference numeral 22, has two arms with a rectangular cross-section and the third 23 has two arms with an oval cross-section, or, as will be appreciated, the with form of said arms varying greatly.

Also in the case of the constriction in the zone 16 shown in FIGS. 1 to 4, the cross-section can assume various specific shapes such as those designated by reference numerals 24 for a half-rod-shaped section, 25 for a circular section, 26 for a substantially rectangular section or 27 for an oval section, or else the shape of said cross-section can vary within wide limits.

The various views show the upper face of the end head 14 with a flat shape, taking into account the fact that said shape is intended to allow the possible joining of a molar tube to allow complementary actions.

Figure 9:
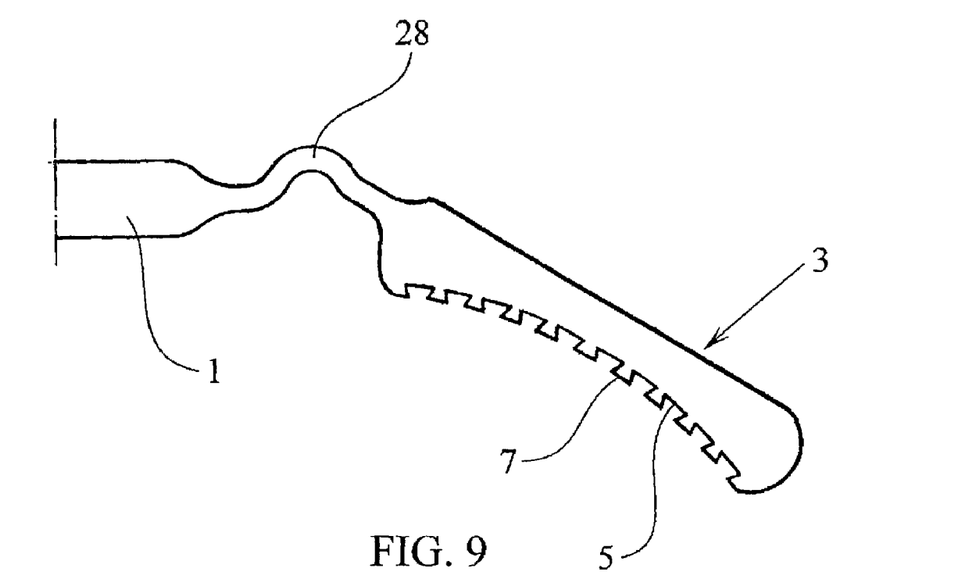

FIGS. 9 to 17 show various additional versions of the flexible zone between the portion of the central element of the device and the zone for adaptation to the molar. Thus, for example, FIG. 9 shows the arrangement, between said central zone 1 and the end zone 3 which can be adapted to the molar, of a singly curved zone 28 which can have a sinusoidal, omega or similar shape.

Figure 10:
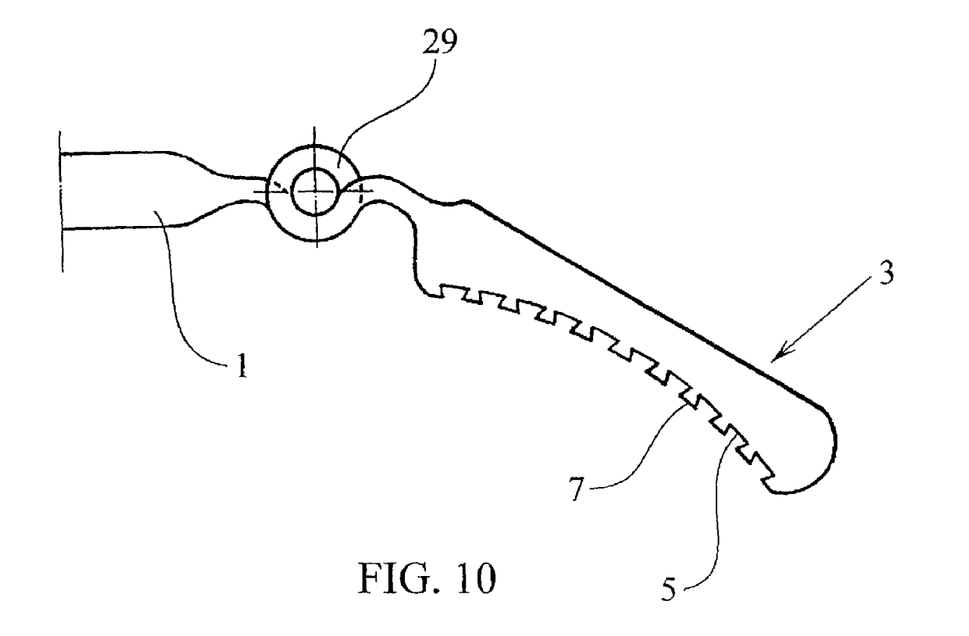

FIG. 10 shows a version in which the zone of greater flexibility consists of a closed curve 29 in the form of an omega or another form.

Figure 11:
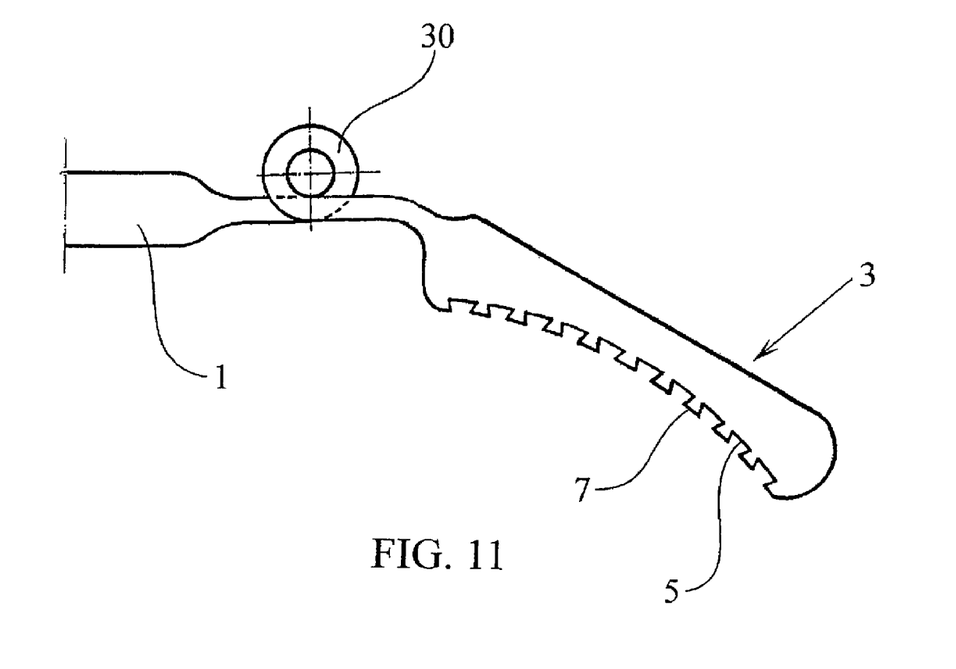
FIGS. 11 and 12 show respective helical versions with one turn.
Figure 12:
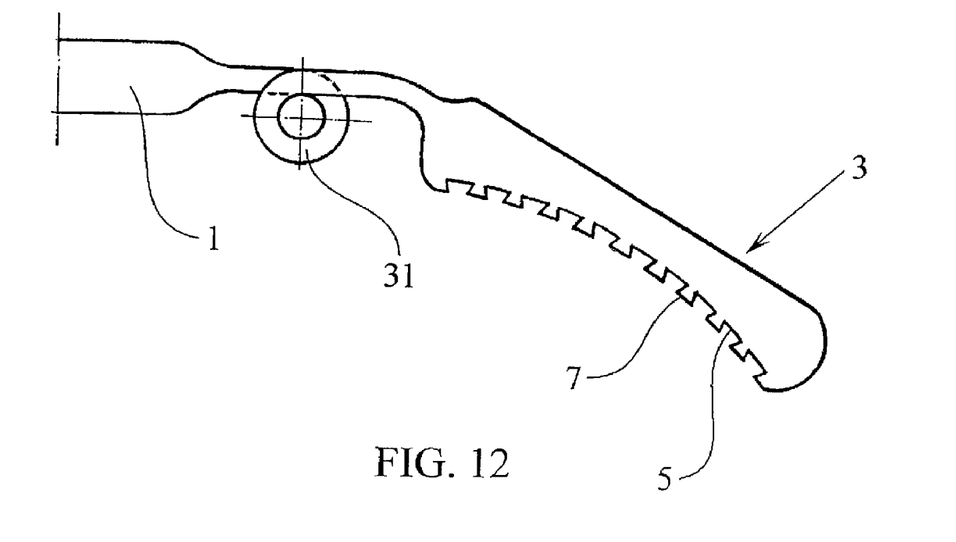

FIGS. 11 and 12 show respective versions 30 and 31 in the form of loops which are directed toward the upper portion and lower portion respectively.

Figure 13:
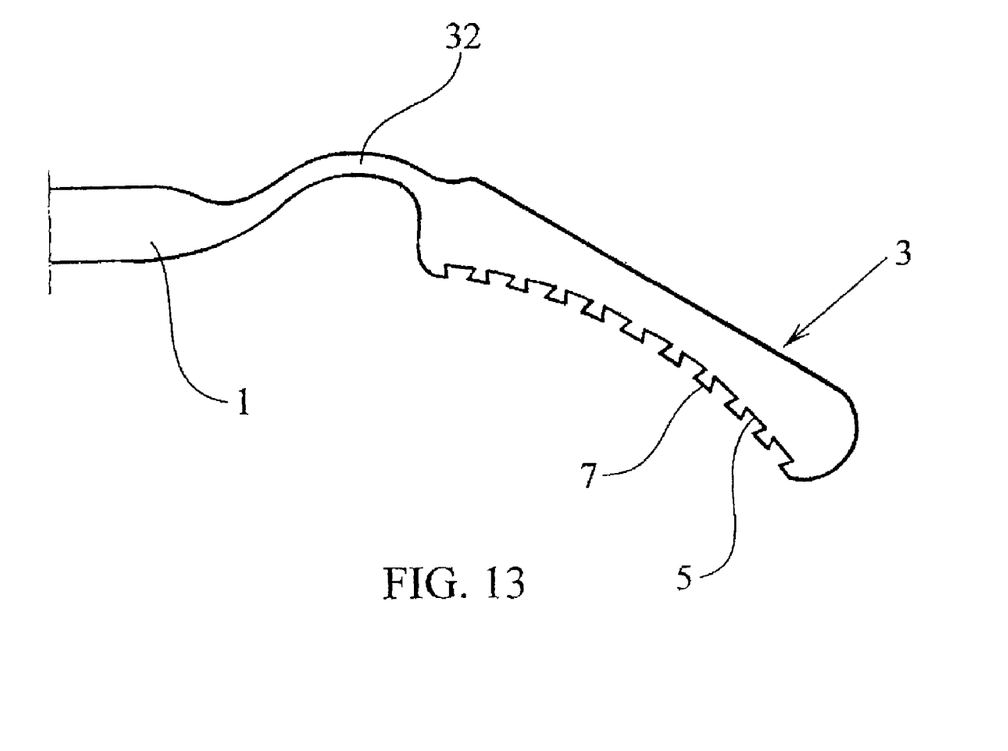
FIG. 13 shows an arrangement in the form of a smooth curve.

FIG. 13 shows a version in which a smooth curved zone 32 is disposed singly between the central portion 1 of the device and the end head for application to the molar.

Figure 14:
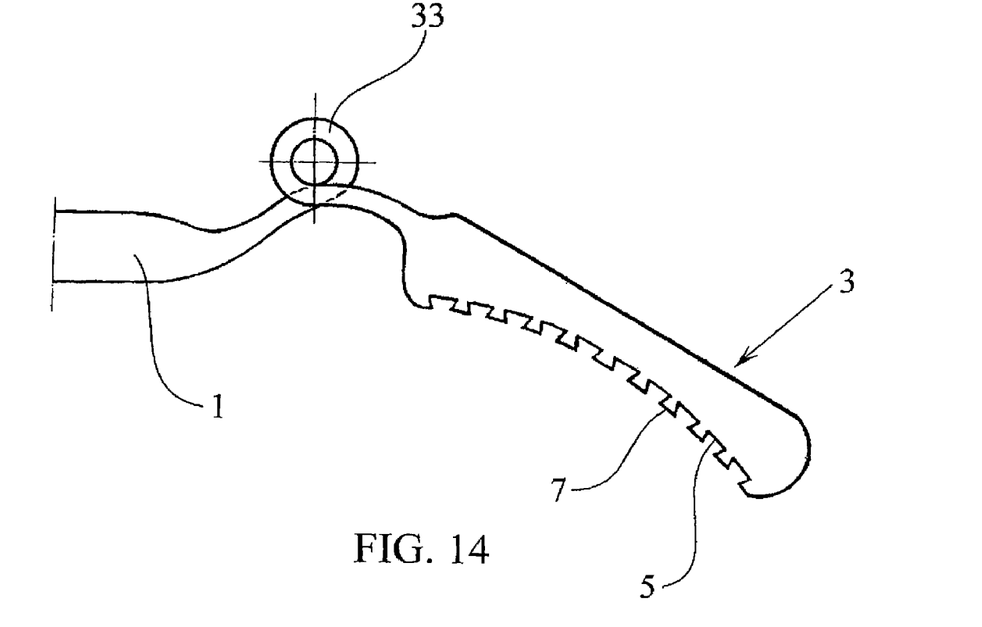
FIGS. 14 and 15 show respective helical shapes in a form similar to a spring in the upper and lower portion respectively.
Figure 15:
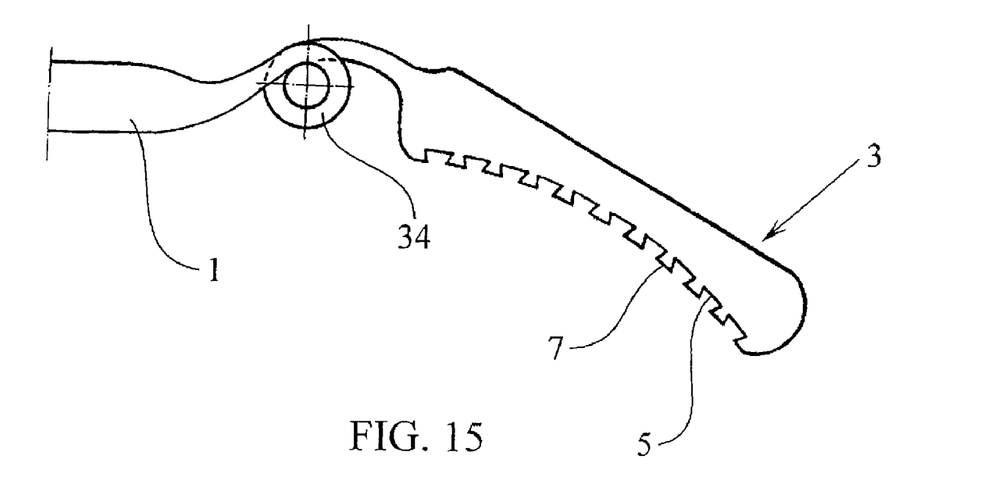

FIGS. 14 and 15 show respective versions in which the zones of greater flexibility 33 and 34 are produced by means of respective elements of helical shape with a plurality of turns, in other words in the manner of a spring, directed upwardly and downwardly respectively.

Figure 16:
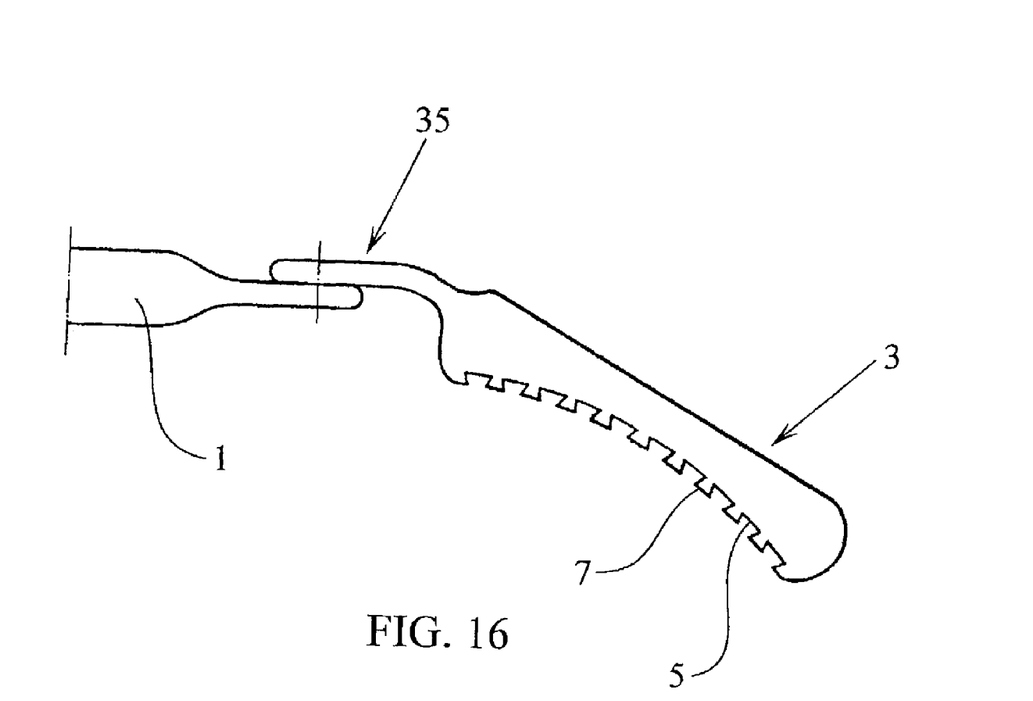
FIGS. 16 and 17 show an arrangement with a loop directed laterally with respect to the positional convention used in the previous figures.
Figure 17:
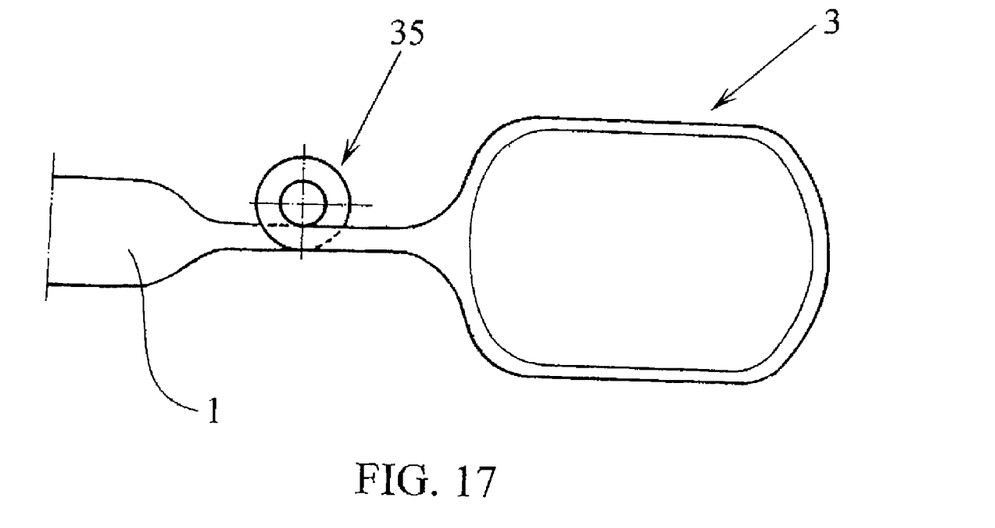

FIGS. 16 and 17 show a lateral elevation and a plan view of an embodiment in which the zone of greater flexibility 35 is formed by a loop or the like situated in a disposition which can be described as lateral, based on the convention employed in the previous figures, in which the loops which, simultaneously with the reduction in cross-section, impart the greatest flexibility are disposed in a plane perpendicular to that of the embodiments shown in the earlier figures. It is obvious that the disposition shown in FIGS. 16 and 17 could be found on either of the sides determined by the longitudinal plane of symmetry. Similarly, although not shown, other planes which are intermediate to those shown could be used for said loops and similar elements.

Although not shown in the figures, the invention will similarly allow the production of the more flexible connection zone, between the central portion of the distalization segment and the head for fixing to the molar, from a metal part made of a more highly adaptable metal such as, for example, stainless steel. In this case, the constriction in said zone of greater flexibility may be omitted since the adaptation can be achieved partially by direct bending of said metal part.

The materials for producing the distalization element according to the present invention can be varied, providing that the mechanical characteristics, in particular adequate toughness and resilience, necessary for the operation thereof are achieved. In particular, a metal material of the type known as super-resilient, steel, thermoelastic materials or a plastics material, for example a polymer, may be provided.

Super-resilient materials include those known as Ni—Ti such as Cu, Ni, Ti and Cr alloys.

The invention claimed is:

1. Segmental distalization element for orthodontic treatments comprising, an elongate monolithic element for orthodontic treatments consisting of:
    a smoothly arcuate central body;
    a first head disposed at a first end of the arcuate body, the first head having a first width greater than a cross section of the central body and being configured for attachment to a canine tooth; and
    a second head having a second width greater than the cross section of the central body and being configured for attachment to a molar tooth,
    wherein the second head is connected to the arcuate body via a zone of greater flexibility, and the zone of greater flexibility is more flexible than the arcuate body so as to increase the resilience of the distalization element in said zone and achieve easy, direct adaptation,
    and wherein the distalization element heads are adapted to canine and molar teeth located only in a same maxillary or mandibulary quadrant.

2. Segmental distalization element for orthodontic treatments according to claim 1, wherein the material for producing the element is a tough resilient material.

3. Segmental distalization element for orthodontic treatments according to claim 1, wherein the zone of greater flexibility is a constricted zone connecting bridge having a smaller cross-section than the remainder of the element.

4. Segmental distalization element for orthodontic treatments according to claim 3, wherein the zone of reduced cross-section has two successive angles, the first angle being between the central arcuate portion of the distalization element and a reduced-section intermediate constricted zone connecting bridge for connection to the second head for attachment to the molar and the second angle being in the actual intermediate bridge before its connection to said second head for adaptation to the molar.

5. Segmental distalization element for orthodontic treatments according to claim 3, wherein the reduction in the cross-section of the bridge for connection to the head for coupling to the molar is obtained by providing a single bridge of reduced cross-section.

6. Segmental distalization element for orthodontic treatments according to claim 3, wherein the constricted zone of the bridge for connection to the second head for attachment to the molar is obtained by providing an aperture or apertures to make the connecting bridge more flexible.

7. Segmental distalization element for orthodontic treatments according to claim 1, wherein the zone of greater flexibility consists of a segment which is singly curved with smooth curvature.

8. Segmental distalization element for orthodontic treatments according to claim 1, wherein the zone of greater flexibility consists of a closed loop.

9. Segmental distalization element for orthodontic treatments according to claim 1, wherein the zone of greater flexibility consists of one or more turns.

10. Segmental distalization element for orthodontic treatments according to claim 4, wherein the angles of the double elbow are obtuse angles.

11. Segmental distalization element for orthodontic treatments according to claim 1, wherein the segmental distalization element is produced from a super-resilient material.

12. Segmental distalization element for orthodontic treatments according to claim 1, wherein the segmental distalization element is produced from a plastics material.

13. Segmental distalization element for orthodontic treatments according to claim 1, wherein the segmental distalization element is produced from thermoelastic material.

14. A segmental distalization element for orthodontic treatments including an elongate element consisting of:
 a smooth arcuate central body;
 a first head disposed at a first end of the central body, the first head having a first width greater than a cross section of the central body and a first internal zone configured for attachment to a maxillary canine tooth;
 a second head having a second width greater than the cross section of the central body and a second internal zone configured for attachment to a maxillary molar tooth; and
 a bridge connecting the second head to a second end of the central body, the bridge having greater flexibility than the central body,
 wherein the elongate element is formed in a single piece and adapted to canine and molar teeth located only in a same maxillary or mandibular quadrant.

15. The segmental distalization element according to claim 14, wherein the bridge has a smaller cross section than the central body.

16. The segmental distalization element according to claim 15, wherein the bridge is connected to the central body at a first angle, and wherein the bridge includes a second angle at an intermediate section thereof.

17. The segmental distalization element according to claim 16, wherein each of the first and second angles are obtuse.

18. The segmental distalization element according to claim 14, wherein the greater flexibility of the bridge is provided by at least one aperture disposed in the bridge.

19. The segmental distalization element according to claim 14, wherein the bridge is curved along a single smooth curvature.

20. The segmental distalization element according to claim 14, wherein the bridge includes a portion having a shape of a closed loop.

21. Segmental distalization element for orthodontic treatments comprising, an elongate monolithic element for orthodontic treatments consisting of:
 a smoothly arcuate central body;
 a first head disposed at a first end of the arcuate body, the first head having a first width greater than a cross section of the central body and being configured for attachment to a first tooth; and
 a second head having a second width greater than the cross section of the central body and being configured for attachment to a second tooth,
 wherein the second head is connected to the arcuate body via a zone of greater flexibility,
 and the zone of greater flexibility is more flexible than the arcuate body so as to increase the resilience of the distalization element in said zone and achieve easy, direct adaptation, and wherein the distalization element heads are adapted to the first tooth and the second tooth located only in a same maxillary or mandibular quadrant.

* * * * *